United States Patent
Chu et al.

(10) Patent No.: US 10,520,694 B2
(45) Date of Patent: Dec. 31, 2019

(54) MEDICAL DEVICES AND RELATED METHODS

(71) Applicant: Boston Scientific Scimed, Inc., Maple Grove, MN (US)

(72) Inventors: Michael S. H. Chu, Brookline, MA (US); Richard C. Tah, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 16/196,550

(22) Filed: Nov. 20, 2018

(65) Prior Publication Data
US 2019/0154937 A1 May 23, 2019

Related U.S. Application Data

(60) Provisional application No. 62/588,979, filed on Nov. 21, 2017.

(51) Int. Cl.
| | |
|---|---|
| *G02B 6/44* | (2006.01) |
| *A61B 1/00* | (2006.01) |
| *A61M 25/09* | (2006.01) |
| *G02B 6/38* | (2006.01) |

(52) U.S. Cl.
CPC ........ *G02B 6/4457* (2013.01); *A61B 1/00064* (2013.01); *A61M 25/09041* (2013.01); *G02B 6/3823* (2013.01)

(58) Field of Classification Search
None
See application file for complete search history.

(56) References Cited

U.S. PATENT DOCUMENTS

| | | | |
|---|---|---|---|
| 5,243,679 | A | 9/1993 | Sharrow et al. |
| 5,730,150 | A | 3/1998 | Peppel et al. |
| 5,827,202 | A | 10/1998 | Miraki et al. |
| 5,843,002 | A | 12/1998 | Pecor et al. |
| 7,120,349 | B2 | 10/2006 | Elliott |
| 7,485,116 | B2 | 2/2009 | Cao |
| 2006/0210230 | A1 | 9/2006 | Kline et al. |
| 2016/0120267 | A1 | 5/2016 | Burns et al. |

FOREIGN PATENT DOCUMENTS

WO WO 00/48664 8/2000

OTHER PUBLICATIONS

International Search Report and Written Opinion issued in International Application No. PCT/US2018/062028, daed Mar. 20, 2019 (12 pages).

*Primary Examiner* — Jerry Rahll
(74) *Attorney, Agent, or Firm* — Bookoff McAndrews, PLLC

(57) ABSTRACT

A medical device may include a spool element, including a channel to receive or store a coiled element, and a handle element. The handle element may be coupled to the spool element and include a lumen that at least partially opens into the channel. The medical device may also include an introducer element coupled to the handle, and relative rotation of the spool element and the handle element may dispense or retract the coiled element from the introducer.

20 Claims, 11 Drawing Sheets

MEDICAL DEVICES AND RELATED METHODS

CROSS-REFERENCE TO RELATED APPLICATIONS

This patent claims the benefit of priority under 35 U.S.C. § 119 to U.S. Provisional Patent Application No. 62/588,979, filed Nov. 21, 2017, which is herein incorporated by reference in its entirety.

TECHNICAL FIELD

Various aspects of the present disclosure relate generally to devices and methods useful in medical procedures. More specifically, the present disclosure relates to devices and methods for dispensing or retracting a medical instrument.

BACKGROUND

Guidewires and optical fibers are used in a wide variety of medical procedures, including urology, neurology, otorhinolaryngology, ophthalmology, gastroenterology, cardiology, and gynecology. Generally, a user may control and deliver a guidewire or an optical fiber from packaged spiral loops, but the guidewires and optical fibers may be difficult to handle. For example, a hydrophilic guidewire may be hydrated and made of polyethylene such that the guidewire may be released from a packaged loop, but, as a result, the guidewire may be slippery and difficult to control. Optical fibers may be sensitive or brittle. Optical fibers are usually packaged such that the entire optical fiber must be removed from the packaging before use, increasing the risk of contamination and damage between the removal from packaging and the use with a patient. Once the optical fiber is removed from the patient, it is also difficult to safely store the optical fiber for reuse during the same procedure without contaminating the optical fiber. Moreover, guidewire and optical fiber dispensers often snag during dispensing or retracting, and may also be cumbersome and difficult to control, increasing the chances of user error, further complicating and prolonging the procedure, and exposing the patient to greater risk.

The devices and methods of the current disclosure may rectify some of the deficiencies described above, and/or address other aspects of the prior art.

SUMMARY

Examples of the present disclosure relate to, among other things, medical devices and methods. Each of the examples disclosed herein may include one or more of the features described in connection with any of the other disclosed examples.

In one example, a medical device may include a spool element, including a channel to receive or store a coiled element, and a handle element. The handle element may be coupled to the spool element and include a lumen that at least partially opens into the channel. The medical device may also include an introducer coupled to the handle, and relative rotation of the spool element and the handle element may dispense or retract the coiled element from the introducer.

The medical device may further include one or more of the following features. The channel may be formed by an inner rim and an outer rim. The handle may include a guide element extending from the lumen and into the channel between the inner rim and the outer rim to guide the coiled element into the introducer. The inner rim may include a groove around an exterior circumference, and the handle may include a retainer element that extends partially into the groove. The spool may further include at least one catch that forms a lock for the coiled element between the catch and an edge of the channel, and a proximal end of the coiled element may be positioned between the catch and the edge of the channel. The spool may include at least one tab, and the at least one tab may extend over a top portion of the channel.

The handle element may include a central opening to receive at least one finger of a user to hold the handle element stationary while manipulating the spool element. The spool may include a crank or a hole crank. A radial exterior of the spool may include knurls. A width of the channel may be less than two times the width of coiled element. The handle may include a radially protruding ring that encloses at least a portion of the channel. The spool may include at least one slot on a side opposite to the protruding ring. The handle may include a biased lock element including extension elements separated by slits. The spool may include at least one window cut through into the channel. The medical device may further include an extension tube between the handle and the introducer, and the introducer may include a tapered portion.

In another example, a medical device may include a spool element including a channel formed by an inner rim and an outer rim, and a handle element including at least one cover portion. The at least one cover portion may include at least one extension portion extending into the channel and abutting the inner rim or the outer rim to couple the handle element to the spool. The outer rim may include at least one slit extending along a portion of the outer rim transverse to the circumference of the outer rim.

The medical device may further include one or more of the following features. The slit of the medical device may extend transverse to the circumference of the outer rim and connect to a circumferential slit. The handle element may include at least two extension portions. A first extension portion may biasedly abut the inner rim, and a second extension portion may biasedly abut the outer rim. The inner rim and outer rim may include grooves into which the first and second extension portions rotatably extend. The medical device may include a coiled element within the channel, and relative rotation of the spool element and the handle element may dispense or retract the coiled element from the medical device. A central portion of the handle element may include a connector coupler. The medical device may further include an optical fiber and an optical fiber connector. The optical fiber connector may be lockably positioned within the connector coupler, and a proximal portion of the optical fiber may extend through one of the slits.

In a further example, a medical device may include an optical fiber and a spooler operably coupled to a ratcheting lever and including a circular extension with a spooler hole extending therethrough. The medical device may also include a disc with a toothed edge and a central pin. The disc may be engageable with the ratcheting lever, and the central pin may include a central hole passing through the central pin. The medical device may also include a return spring positioned within the circular extension positioned between the spooler and the central pin. The optical fiber may be looped around an external portion of the disc, and a portion of the optical fiber may pass through the spooler hole and the central hole.

The medical device may further include one or more of the following features. The medical device may further include a spooler cone pin attached to the spooler, and a distal portion of the optical fiber may pass through the spooler cone pin. The disc may further include a smooth edge extending parallel to the toothed edge. A portion of the optical fiber may be housed within a groove formed between the toothed edge and the smooth edge of the disc, and a portion of the optical fiber may extend proximal to the groove such that the optical fiber is connectable to an energy source remote from the medical device. The medical device may further include a slitted tube and a zipper. The zipper may include a guide portion through which a portion of optical fiber extends to move distally or proximally.

Both the foregoing general description and the following detailed description are exemplary and explanatory only and are not restrictive of the features, as claimed. As used herein, the terms "comprises," "comprising," "having," including," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of a stated value.

BRIEF DESCRIPTION OF THE DRAWINGS

The accompanying drawings, which are incorporated in and constitute a part of this specification, illustrate various exemplary embodiments and together with the description, serve to explain the principles of the disclosure.

DETAILED DESCRIPTION

Examples of the present disclosure include devices and methods to facilitate and improve the efficacy, efficiency, and safety of dispensing medical devices during medical procedures. For example, aspects of the present disclosure may provide a user (e.g., a physician, medical technician, or other medical service provider) with the ability to more easily dispense and retract a guidewire or an optical fiber to be delivered within a patient and/or through an insertion device. Some aspects of the present disclosure may be used in performing an endoscopic, hysteroscopic, or ureteroscopic procedure.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or an insertion device. When used herein, "proximal" refers to a position relatively closer to the exterior of the body or closer to an operator using the medical device or insertion device. In contrast, "distal" refers to a position relatively farther away from the operator using the medical device or insertion device, or closer to the interior of the body.

Figure 1:
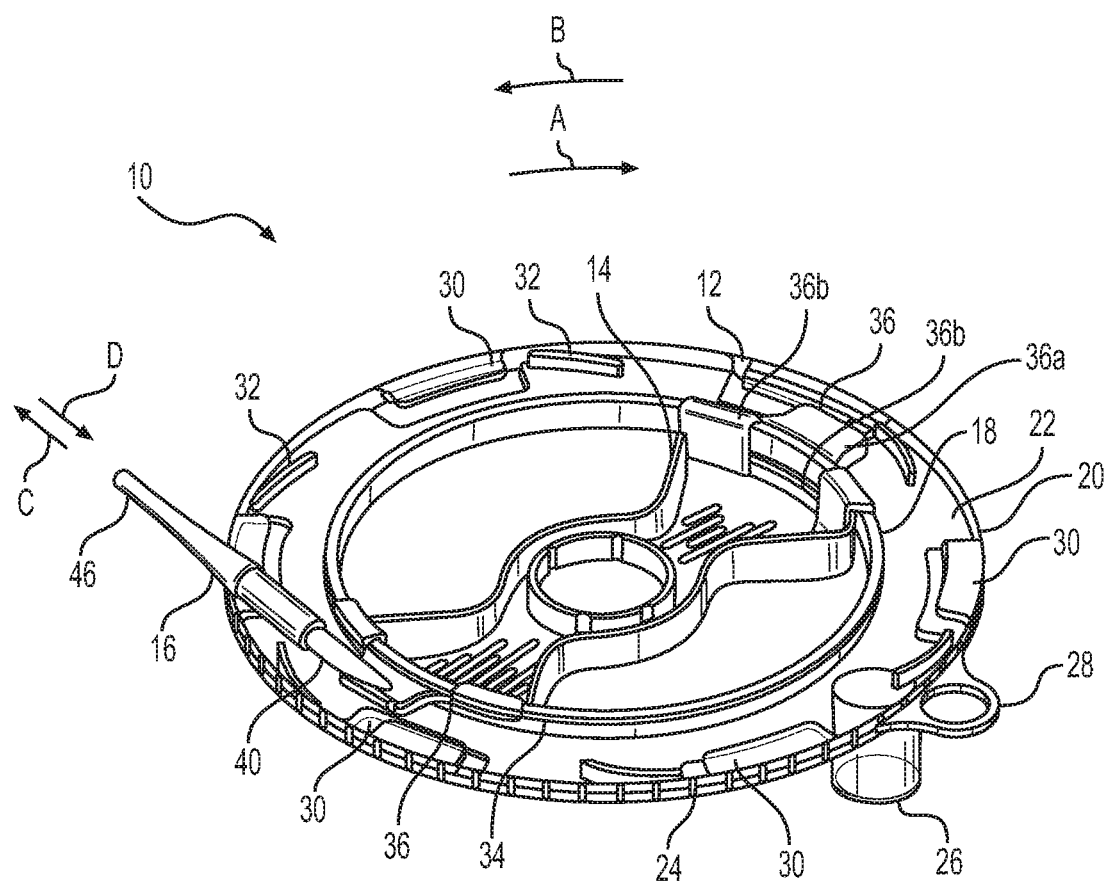
FIG. 1 illustrates a medical device, according to aspects of the present disclosure.

FIG. 1 illustrates a medical device 10 that includes a spool 12 and a handle 14. Medical device 10 may also include an introducer 16 coupled to at least one of spool 12 and handle 14. Spool 12 may include an inner rim 18 and an outer rim 20, with inner rim 18 and outer rim 20 forming a channel 22 to receive or store a coiled element, such as a guidewire, optical fiber, or other medical elements. Spool 12 and handle 14 may be rotatably coupled such that relative rotation of spool 12 and handle 14 either dispenses or retracts the coiled element.

Figure 2:
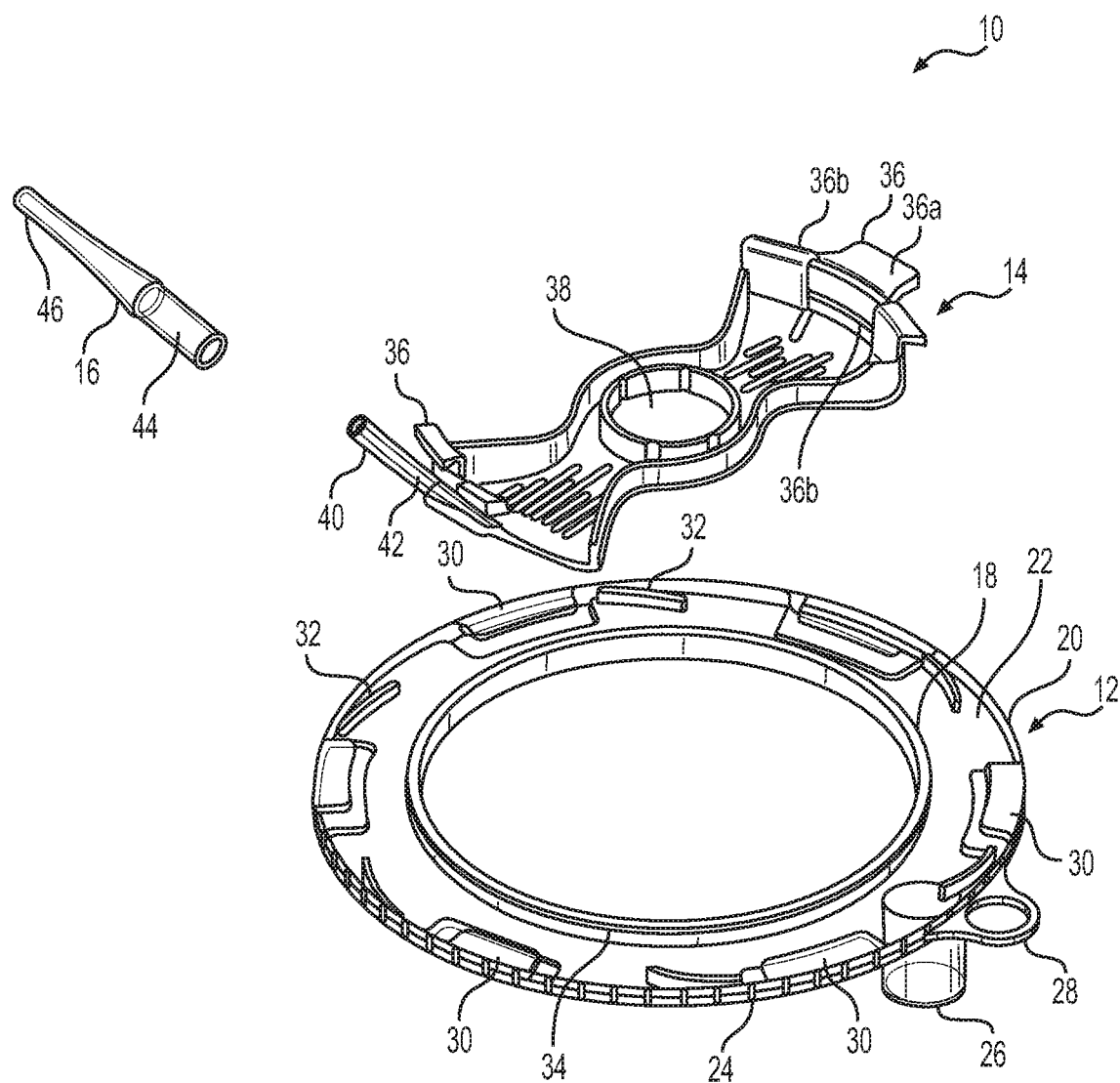
FIG. 2 illustrates an exploded view of the medical device of FIG. 1, according to aspects of the present disclosure.

FIG. 2 shows an exploded view of medical device 10. As shown in both FIGS. 1 and 2, spool 12 may be substantially circular with a radial thickness and a vertical thickness. Spool 12 may include knurls 24 on an outer circumferential surface. Knurls 24 may allow a user to securely grip and manipulate spool 12. Spool 12 may also include a crank 26 and/or a hole crank 28 positioned on a top, a bottom, or a lateral side of spool 12. Crank 26 or hole crank 28 may allow a user to more quickly or efficiently rotate spool 12 relative to handle 14. Although not shown, medical device 10 may include or be coupled to a motor or other mechanical device to operate crank 26 or hole crank 28.

Spool 12 may include a plurality of tabs 30 extending radially inward from a top edge of outer rim 20. Tabs 30 may hold the coiled element in channel 22, while still allowing the coiled element to slide within channel 22. Spool 12 may further include at least one catch 32, which may securely hold a proximal end of the coiled element in a locked position between the at least one catch 32 and inner rim 18 or outer rim 20. The at least one catch 32 may be a curved protrusion positioned near outer rim 20, and may help to ensure that the coiled element is securely held within spool 12 during the dispensing or retraction. As shown, a plurality of catches 32 may be positioned at different angular positions within channel 22. Alternatively, spool 12 may only include one or two catches 32 within channel 22. Although not shown, spool 12 may further include arrows or other indicators that may aid a user in determining the appropriate direction of rotation to either dispense or retract the coiled element.

Handle 14 may be removably coupled to spool 12, and may fit within a radial inner portion of spool 12. Inner rim 18 of spool 12 may form a groove or track 34, and handle 14 may include radially outward extending retainers 36. For example, handle 14 may include two retainers 36 positioned approximately 180 degrees apart, and retainers 36 may be snap-fit into track 34 such that handle 14 may be secured to, but still rotate relative to spool 12. In one aspect, retainer 36 may include an extension 36a that may be positioned on rim 18 and extend to tab 30 to help retain the coiled element within channel 22. Retainer 36 may also include one or more assembly tabs or assembly clips 36b that may be positioned on and/or snap fit on the top or bottom surface of spool 12. It is noted that a portion of one retainer 36 in FIG. 2 is omitted such that additional features of handle 14 may be shown. Handle 14 may also include a central opening 38, which may allow a user to hold handle 14 with a finger positioned within central opening 38. In another aspect, central opening 38 may be sized and shaped to couple medical device 10 to an additional element, for example, an insertion device.

Handle 14 may further include a guide 40 with a lumen 42 extending through guide 40. A distal end of the coiled element may extend through lumen 42 of guide 40. As shown in FIG. 2, guide 40 may extend into channel 22 such that the coiled element may include a distal portion extending into lumen 42 of guide 40 while still within channel 22. As a user rotates one or both of spool 12 and handle 14, the coiled element will either dispense distally or retract proximally through lumen 42 of guide 40 based on the direction of the rotation.

Medical device 10 may optionally include introducer 16 with an introducer lumen 44 (FIG. 2). It is noted that FIG. 2 illustrates introducer 16 as a separate element that may be coupled to a distal end of guide 40, but introducer 16 may also be integrally formed with guide 40. Introducer 16 may protect a distal portion of the coiled element. Introducer 16 may include a tapered portion 46, for example, in a distal portion. As such, introducer 16 may be inserted through a seal (e.g., a Urolok™ Adaptor seal by Boston Scientific Corp.), and the coiled element may be dispensed or retracted through the seal based on the relative rotation of spool 12 and handle 14 with a reduced risk of back-flow of internal fluid or irrigation fluid. Alternatively, introducer 16 may be a fitting (i.e., a male luer, threaded luer, rotating luer connector, etc.), which may be used to attach and introduce medical device 10 to an insertion device via, for example, a T-connector, female luer, etc.

In use, medical device 10 includes a coiled element, such as a guidewire, optical fiber, or another medical element. The below will discuss a guidewire, but it is understood that the discussion equally applies to an optical fiber or another medical element. The guidewire may be wound in channel 22 to form a coil, with a proximal end securely held by at least one catch 32, and a distal end positioned within guide 40 or introducer 16. The guidewire may be looped within channel 22, and may be looped in a single plane, or may be spirally looped. In order to dispense the guidewire, a user may hold handle 14 stationary and may rotate spool 12 in direction A (FIG. 1) such that the guidewire will dispense from medical device 10 in direction C. The user may rotate spool 12 in direction B in order to retract the guidewire in direction D back into medical device 10. The user may hold handle 14 with a finger of either hand positioned within central opening 38, and may rotate spool 12 with the user's thumb acting on knurls 24. Alternatively, the user may hold handle 14 stationary, and may rotate spool 12 with action on crank 26 or hole crank 28. Furthermore, a user may hold handle 14 and pull a distal portion of the guidewire to extend the guidewire from spool 12, which will also cause spool 12 to rotate.

It is noted that catch 32 serves to ensure that the guidewire remains attached to spool 12 such that the guidewire may be retracted. It is further noted that the guidewire may be dispensed, retracted, and then dispensed again during the same medical procedure. Additionally, medical device 10 may be used to retract a guidewire that is not attached to catch 32, for example, if the guidewire is fully dispensed and separate from medical device 10. The user may "inch" the guidewire through introducer 16 using the user's fingers, and then the user may rotate spool 12 in direction B to continue retracting the guidewire. The guidewire may be feed through or otherwise secured to one of catches 32, or the physical properties of the guidewire may allow for friction between the proximal end of the guidewire within channel 22 such that rotation of spool 12 withdraws and retracts the guidewire. In one aspect, guidewire may include a super elastic core such that, as the guidewire is inserted into spool 12, the guidewire tends to straighten due to the elastic properties. As the guidewire is inserted into spool 12, the proximal end of the guidewire will continue to move around outer rim 20 until the proximal end encounters catch 32 and is directed toward the narrow portion between catch 32 and outer rim 20 that may be sized to grip the diameter of the inserted guidewire. If the user continues to insert the guidewire, the guidewire will be fit between catch 32 and outer rim 20, causing spool 12 to move relative to guidewire and the guidewire to begin forming a spiral loop within channel 22.

In some aspects, medical device 10 may be designed and/or used to dispense a particular type or size of guidewire (e.g., a Navipro™ guidewire, a Zipwire™ guidewire, or a Jagwire™ guidewire, all by Boston Scientific Corp.). The guidewire may include a nitinol core, and may include a hydrophilic coating depending on the particular use. In one aspect, the guidewire may be not hydrated before dispensing to provide a non-slip handling grip. Moreover, both spool 12 and handle 14 may be made of injection molded plastic, and may be made of a clear, translucent, or opaque polymer. If the elements are clear, medical device 10 may allow a user to visually inspect the status and/or supply of the guidewire remaining on spool 12 or to see through introducer 16 as the guidewire is being loaded into or dispensed from medical device 10. The elements may be glued, press fit, snap fit, or otherwise coupled together.

Figure 3:
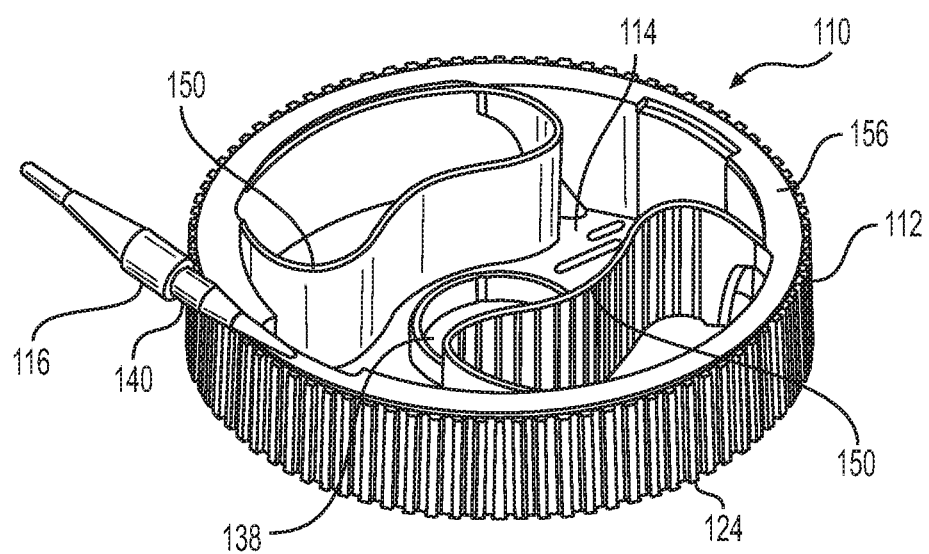
FIG. 3 illustrates an additional medical device, according to aspects of the present disclosure.
Figure 4B:
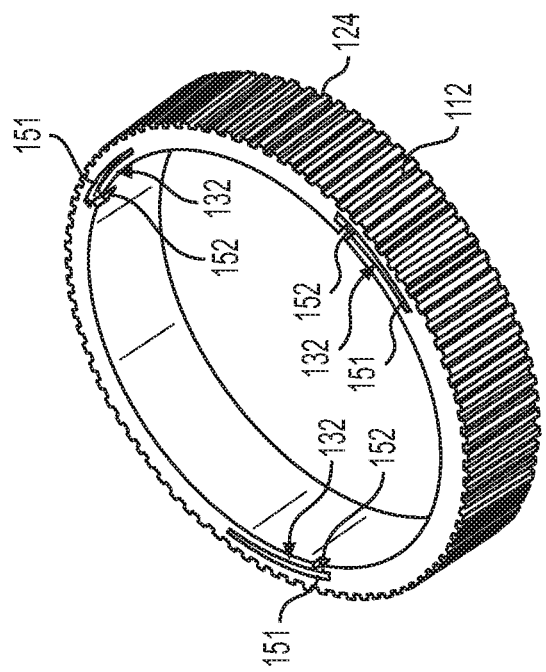
FIG. 4B illustrates a perspective view of a portion of the medical device of FIG. 3, according to aspects of the present disclosure.
Figure 4A:
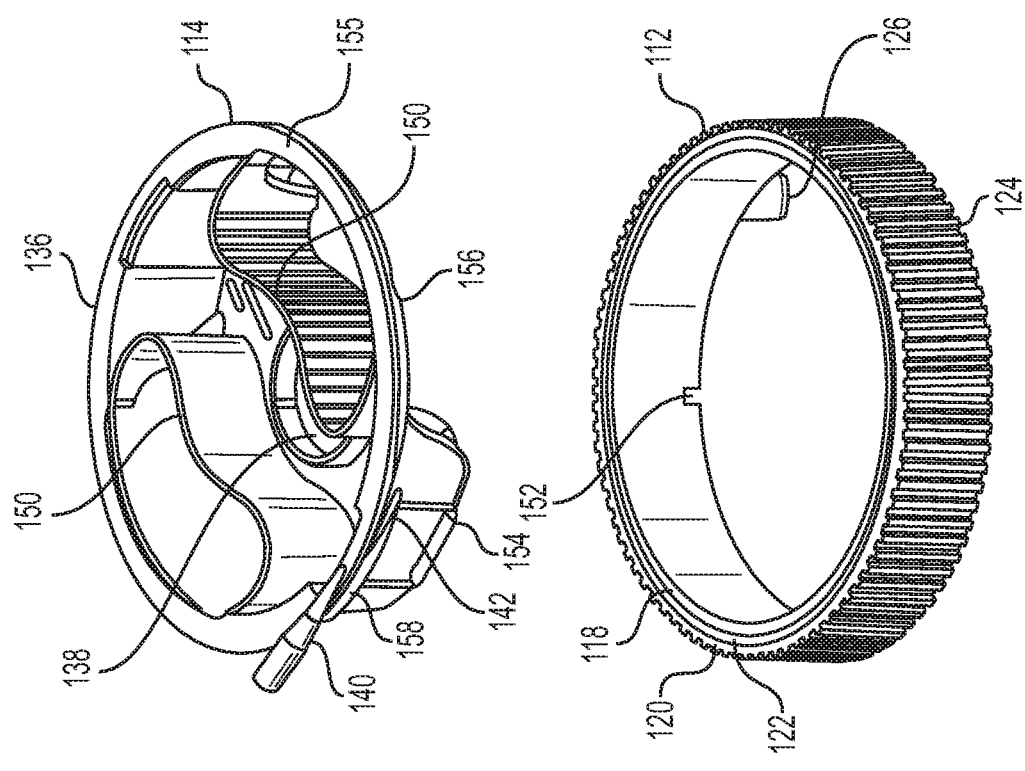
FIG. 4A illustrates an exploded view of the medical device of FIG. 3.

FIGS. 3, 4A, 4B, and 5 illustrate an alternative example with similar elements to medical device 10 shown by 100 added to the reference numbers. This aspect illustrates a medical device 110 with a spool 112, a handle 114, and an introducer 116. As shown in FIGS. 3, 4A, and 4B, spool 112 and handle 114 have a greater vertical thickness than spool 12 and handle 14 of FIGS. 1 and 2. Spool 112 may include ridges or knurls 124 on a radially exterior of spool 112, which may aid in a user's rotation of spool 112. Handle 114 may include a central opening 138, which may be sized to receive a user's finger or to couple medical device 110 to an insertion device or other device. Handle 114 may also include grip extensions 150, which may be ridged and may further aid in a user holding medical device 110. Medical device 110 may be useful for rapidly dispensing and retracting long endoscopy guidewires.

As shown in FIG. 4A, spool 112 includes an inner rim 118 and an outer rim 120 to form a channel 122. Channel 122 may be thinner than channel 22 of FIGS. 1 and 2. For example, channel 122 may be slightly wider than the thickness of the coiled element to be stored and dispensed from medical device 110. In another example, channel 122 may be twice the width of the coiled element to be received, stored, and dispensed from medical device 110. As such, the coiled element may be stacked in a helical or vertical spiral within channel 122. Channel 122 may minimize the recoil of the coiled element, which may reduce the risk of entanglement or kinking during spooling and may increase the ease and speed with which the coiled element may be dispensed and retracted.

Spool 112 may include a crank 126 or a hole crank (not shown). FIG. 4B illustrates a bottom view of spool 112, with crank 126 omitted for clarity. As shown, spool 112 may also include one or more catches 132 to secure a proximal end of the coiled element, for example, at a bottom of channel 122. In one example, spool 112 may include three catches 132, and each catch may be a curved tapered slot 151 with an opening hole 152 extending from inside channel 122 to allow the coiled element to be secured external to channel 122 within catch 132. Each catch 132, including the slot 151 and hole 152 may be sized such that a coiled element may be secured by friction when wedged in slot 151 or hole 152.

Referring to FIGS. 4A and 4B, a user may slide the proximal portion of the coiled element to be removed from slot 151 or hole 152 in order to adjust the length of the proximal portion that extends proximal to medical device 110 and then reposition the proximal portion in slot 151 or hole 152. As such, a user may access and adjust the proximal portion of the coiled element. For example, the coiled element may be a double end guidewire. Alternatively, an optical fiber may be extended proximal of medical device 110 and connected to a laser energy or illumination source. In one aspect, rotation of spool 112 in a first direction may dispense the coiled element proximally, and rotation in a second direction may retract the proximal portion distally interior to spool 112. It is understood that the size of catch 132, including slot 151 and hole 152, may vary based on the type and size of the coiled element. Alternatively, catch 132 may be entirely internal to spool 112 (as shown in FIGS. 1 and 2) in instances where access to and adjustment of the proximal portion is not necessary, for example, when dispensing a single end guidewire.

Handle 114 may connect to spool 112 in a similar manner as discussed with respect to FIGS. 1 and 2. As shown in FIGS. 3 and 4A, handle 114 may include assembly clips 154. As shown in FIG. 4A, a cover 155 may extend radially outward from a top portion of handle 114 and may extend over at least a portion of channel 122. A protrusion ring 156 extends downward, for example, from cover 155, into at least a portion of channel 122, and may ensure that the coiled element cannot escape channel 122. Assembly clips 154 may extend downward and radially inward of spool 112. Assembly clips 154 may include a radially outwardly biased extension positioned opposite from protrusion ring 156. Spool 112 may include a groove or ledge (not shown) to receive a portion of assembly clips 154, or assembly clips 154 may couple to a bottom portion of spool 112. It is noted that the groove, ledge, or other coupling for spool 112 and handle 114 may extend across the entire inner or bottom circumference of spool 112 such that spool 112 and handle 114 may freely rotate relative to each other. Alternatively, the groove, ledge, or other coupling may include gaps or extensions within the circumference that may provide access for a tool or other user manipulation.

Handle 114 includes a guide 140 to connect channel 122 to introducer 116 through lumen 142. Handle 114 may also include a scoop 158, which may extend lumen 142 into channel 122. Scoop 158 may ensure that the coiled element continuously and easily dispenses from or retracts into channel 122. Scoop 158 may also allow the user to "re-channel" the coiled element back into guide 140 in a case where the user over-retracts the coiled element into channel 122.

Figure 5:
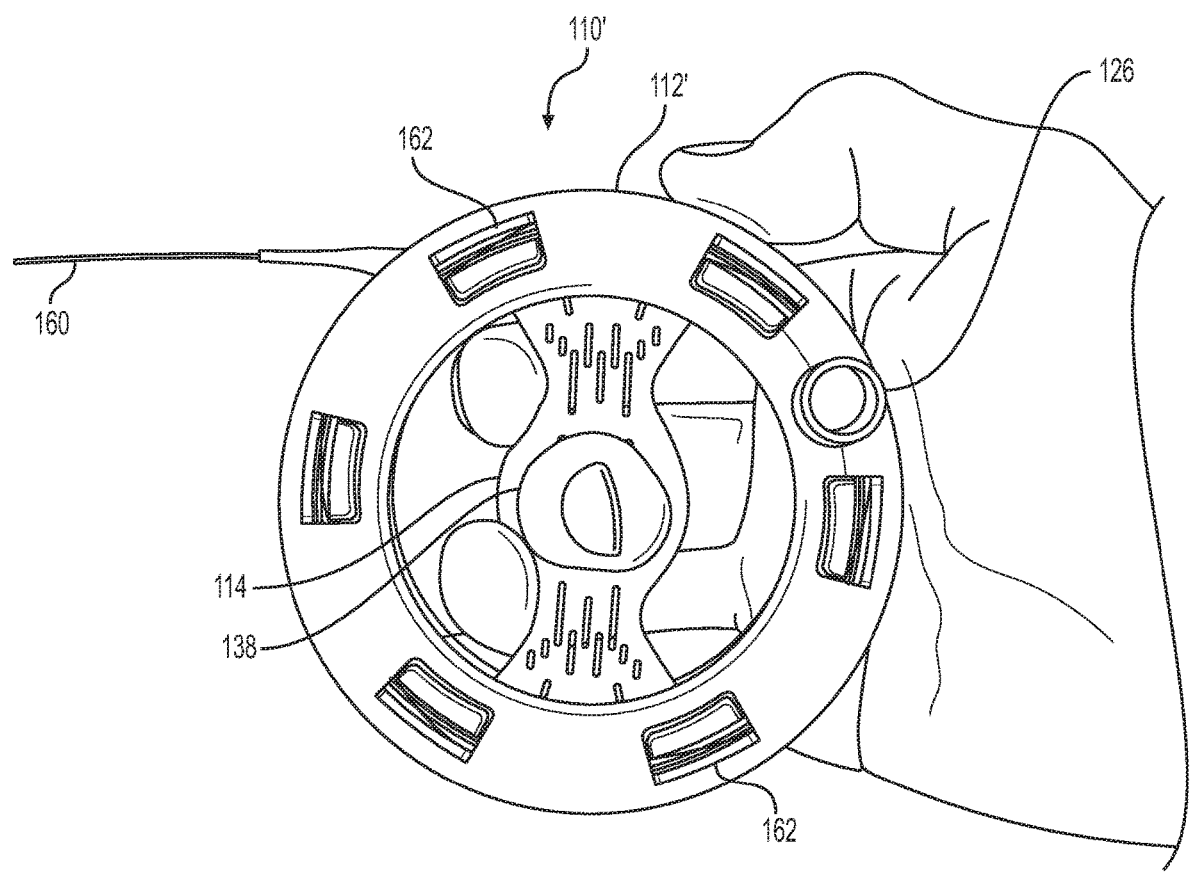
FIG. 5 illustrates a side view of a further medical device being held by a user, according to aspects of the present disclosure.

FIG. 5 illustrates how a user may hold and manipulate a medical device 110', which is similar to medical device 110 discussed above. FIG. 5 shows the user holding medical device 110' in his or her right hand, but it is noted that medical device 110' could equally be held in a user's left hand. As shown, the user may position his or her middle finger in central opening 138 of handle 114, and may position other fingers on one or both sides of handle 12. Using his or her thumb, the user may rotate spool 112' to dispense or retract a guidewire 160. Alternatively or additionally, the user may use his or her other hand to operate crank 126 to dispense or retract guidewire 160 more quickly. In another aspect, the user may use his or her other hand to grasp the distal end of guidewire 160 and pull the distal end distally to dispense guidewire 160. Spool 112' may be transparent and/or may include window portions 162 cut into spool 112' to allow the user to see into the channel and observe how much of the guidewire 160, optical fiber, or other coiled medical element remains internal to spool 112.

Figure 6:
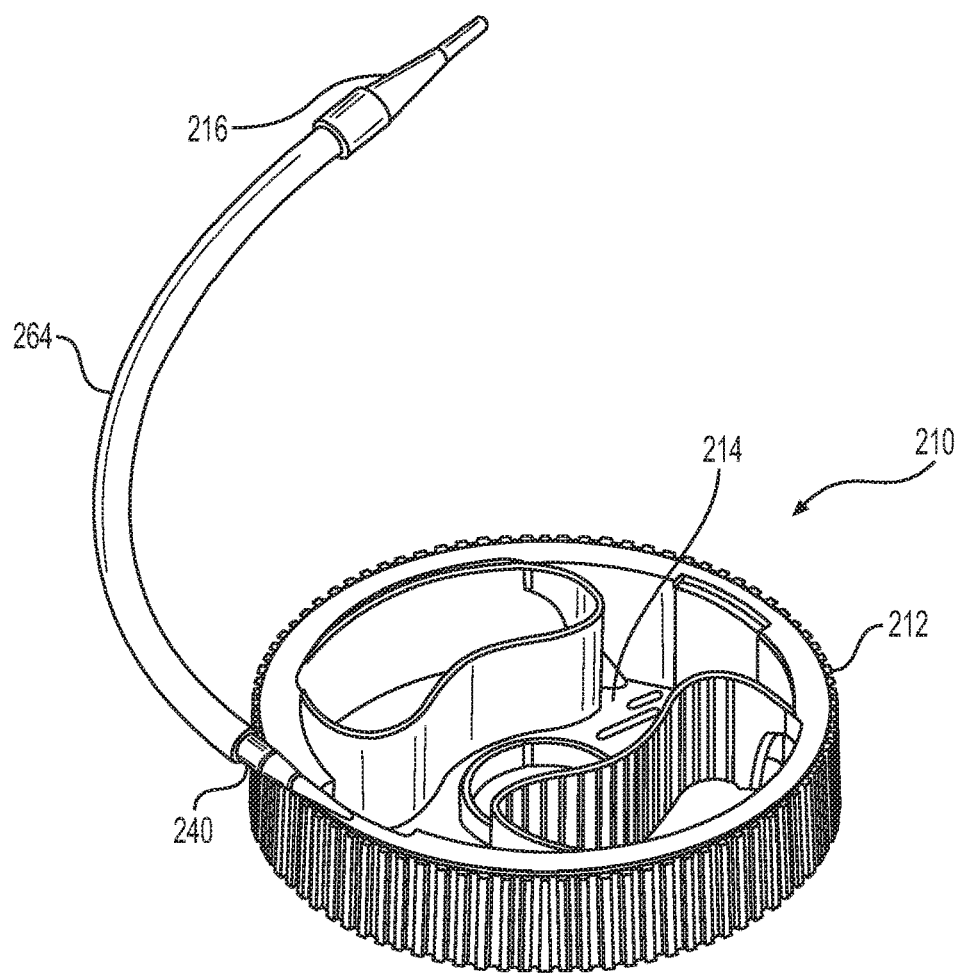
FIG. 6 illustrates an additional aspect of a medical device, according to aspects of the present disclosure.

FIG. 6 illustrates an alternative example with similar elements to medical device 10 shown by 200 added to the reference numbers. This aspect illustrates a medical device 210 with a spool 212, a handle 214, and an introducer 216. In addition, medical device 210 includes an extension tube 264. Extension tube 264 extends from guide 240 to introducer 216. Extension tube 264 may help to prevent overwinding a guidewire or other coiled medical element. For example, a user may wind the coiled element and stop the winding with the distal tip of the coiled element within extension tube 264. As such, the coiled element is ready to be dispensed again, and is also protected from damage even though the coiled element is external to the channel. Extension tube 264 may also extend the reach of medical device 210. That is, spool 212 and handle 214 may be positioned a greater distance away from the patient, the insertion device, etc. than a medical device without extension tube 264. Furthermore, extension tube 264 may help prevent the coiled element from kinks and other damage.

Figure 7:
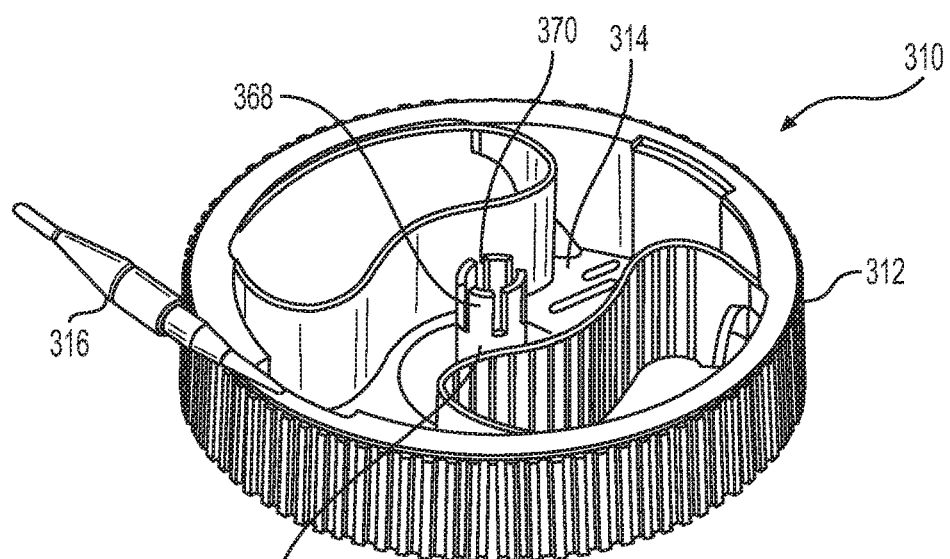
FIG. 7 illustrates another additional aspect of a medical device, according to aspects of the present disclosure.

FIG. 7 illustrates an alternative example with similar elements to medical device 10 shown by 300 added to the reference numbers. This aspect illustrates a medical device 310 with a spool 312, a handle 314, and an introducer 316. In addition, medical device 310 includes a biased lock 366. Biased lock 366 may be positioned in a central portion of handle 314, and may allow for a connector element to be temporarily or removably coupled to medical device 310. As shown, biased lock 366 may include a plurality of extensions 368 separated by slots 370. For example, extensions 368 and slots 370 may extend a portion of the vertical thickness of handle 314. Extensions 368 may flex to couple a connector element to handle 12.

Figure 8:
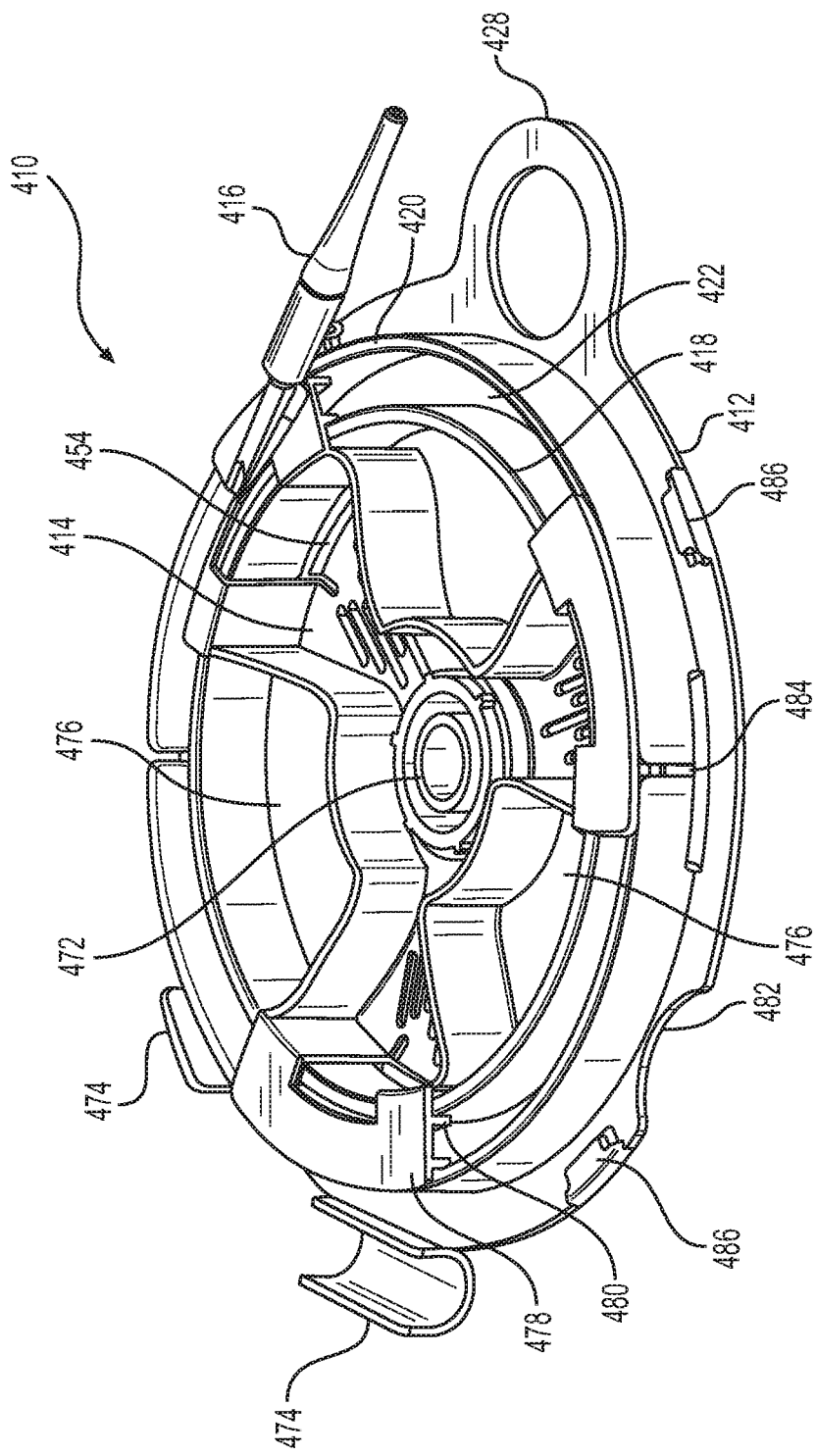
FIG. 8 illustrates a further exemplary medical device, according to aspects of the present disclosure.
Figure 9:
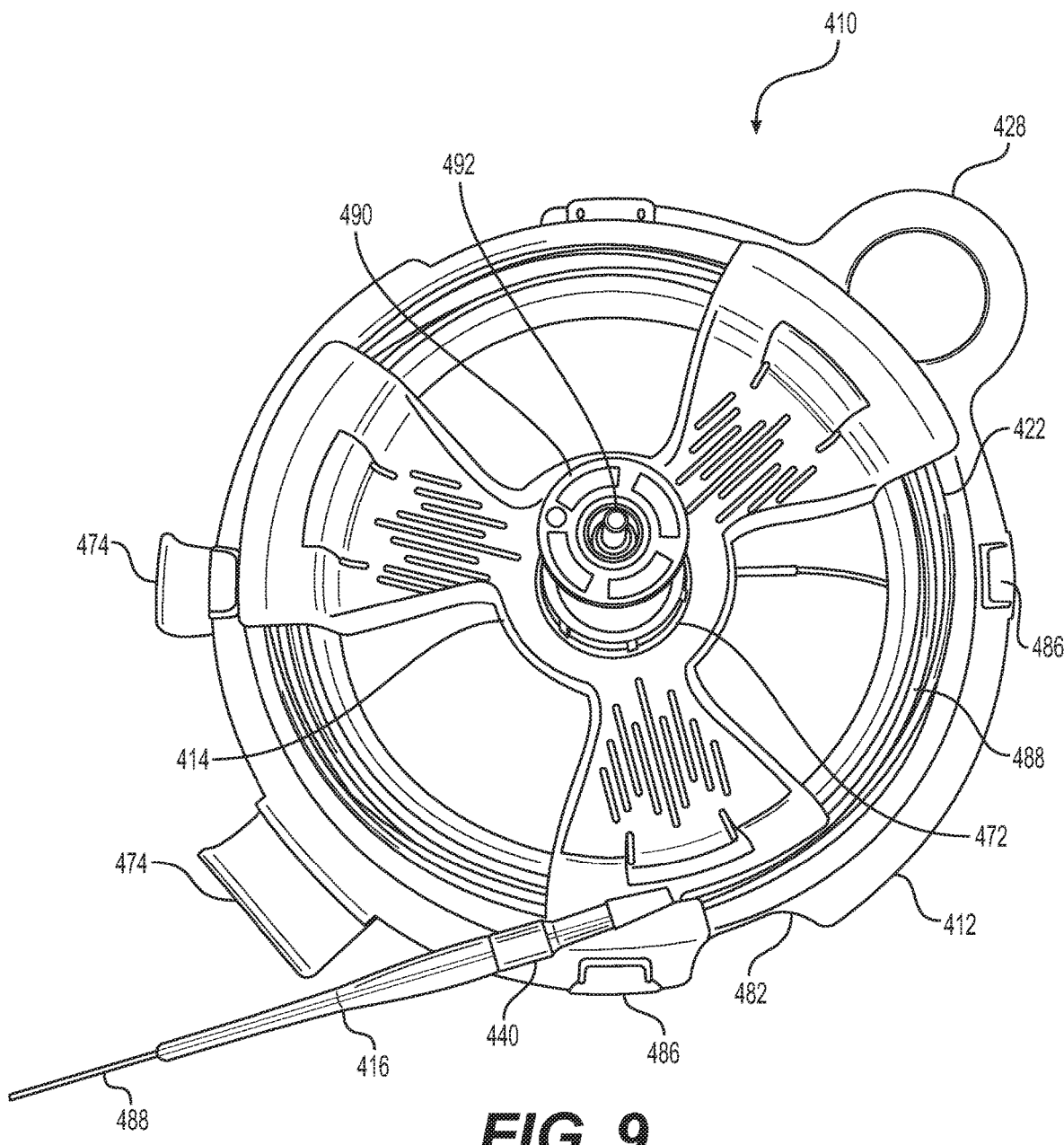
FIG. 9 illustrates a top view of an additional medical device, according to additional aspects of the present disclosure.
Figure 10:
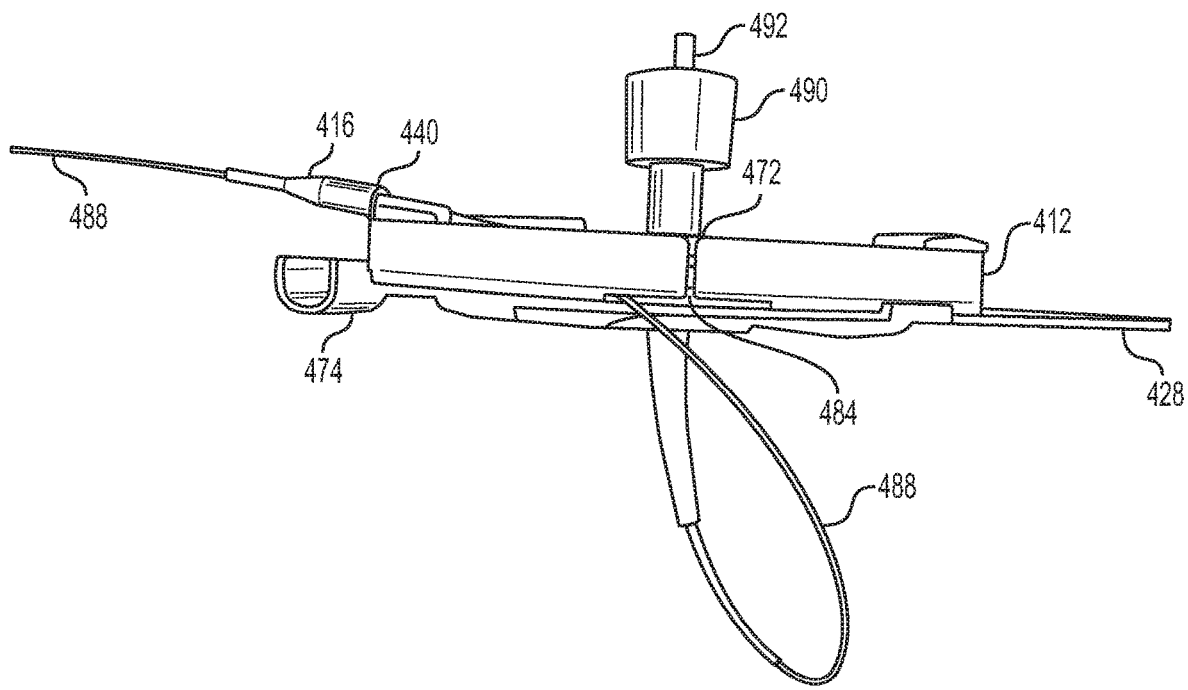
FIG. 10 illustrates a side view of the medical device of FIG. 9, according to additional aspects of the present disclosure.

FIGS. 8-10 illustrate a further alternative example with similar elements to medical device 10 shown by 400 added to the reference numbers. FIG. 8 illustrates a medical device 410 with a spool 412, a handle 414, and an introducer 416. In addition, medical device 410 includes a coupler 472 in a central portion of handle 414. Coupler 472 may removably receive a connector element for a coiled element. Medical device 410 may also include one or more connector clips 474 extending from a radial outer portion of spool 412, and connector clips 474 may also removably receive the connector element. For example, the connector element for the coiled element may be coupled to coupler 472 in a position transverse to a plane of spool 412 (FIGS. 9 and 10), or the connector element may be coupled to connector clips 474 within or parallel to the plane of spool 412. Coupler 472 and connector clips 474 may be adjustable and/or sized to receive different sized connector elements. In one aspect, coupler 472 may be sized to receive one connector element, and connector clips 474 may be sized to receive different connector elements.

Spool 412 may also include a channel 422 between an inner rim 418 and an outer rim 420 to receive the coiled element. Handle 414 may include one or more openings 476 to allow a user to hold handle 414. Handle 414 may also include a plurality of covers 478 with extension members 480 to couple handle 414 to spool 412. Covers 478 may extend over channel 422, and extension members 480 may function similar to protrusion ring 156 of FIG. 4A and extend partially into a portion of channel 422. Extension members 480 may abut and/or be biased toward inner rim 418 and outer rim 420, respectively, and couple handle 414 to spool 412. Additionally, inner rim 418 and/or outer rim 420 may include grooves or retainer surfaces into which a portion of extension members 480 may be secured to rotatably couple handle 414 to spool 412. Although covers 478 and extension members 480 are shown only extending over a portion of channel 422, it is noted that covers 478 and extension members 480 may also extend over the entirety of channel 422. Moreover, handle 414 may include one or more assembly clips 454 to couple handle 414 to spool 412 as discussed above.

Spool 412 may also include a crank (not shown), a hole crank 428, and/or an indented portion 482 to allow a user to manipulate spool 412 relative to handle 414 to dispense or retract a coiled element. Although not shown, a radially outermost portion of spool 412 or the outer portion of outer rim 420 may include knurls or a gripping surface to aid a user to manipulate spool 412.

Furthermore, outer rim 420 may include one or more entry/exit ports or slits 484. In one aspect, outer rim 420 may include one or more slits 484 positioned evenly or unevenly in outer rim 420. Slits 484 may extend through a portion of outer rim 420 transverse to the circumference of outer rim 420. Slits 484 may also include a circumferential slit that partially extends through a bottom portion of spool 412 radially outside of outer rim 420. Slits 484 may allow for the coiled element to be introduced into or removed from channel 422. Spool 412 may also include one or more fiber clips 486 to secure a portion of the coiled element that extends radially outside of outer rim 420. The one or more fiber clips 486 may be positioned in proximity to the one or more slits 484. FIG. 8 shows fiber clips 486 positioned on a top portion of spool 412, but it is noted that fiber clips 486 may alternatively or additionally be positioned on a bottom portion of spool 412.

FIG. 9 is a top view of medical device 410 coupled to an optical fiber 488 and an optical fiber connector 490. FIG. 10 is a side view of medical device 410 coupled to optical fiber 488 and optical fiber connector 490. Optical fiber connector 490 includes a proximal end connector 492 to connect optical fiber 488 to an energy source, for example, a laser energy source or an illumination energy source, with the energy to be delivered through optical fiber 488 to an internal lumen of a patient. Rotation of spool 412 relative to handle 414 dispenses or retracts optical fiber 488 through introducer 416 and guide 440. While the discussion of these figures focuses on an optical fiber, it is noted that the disclosed aspects may also be applied to other medical devices, such as, guidewires, catheters with one or more lumens, filaments, cables, etc.

As shown in FIG. 9, optical fiber connector 490 may be positioned within coupler 472. As shown in FIG. 10, a portion of optical fiber connector 490 may extend through coupler 472. A portion of optical fiber 488 may then extend from optical fiber connector 490 and through one of slits 484 in outer rim 420 of spool 412 to enter channel 422. Although not shown, optical fiber 488 may be positioned within one or more of fiber clips 486 to form a circular or spiral orientation. Optical fiber 488 may be looped through channel 422 any number of times based on the length of optical fiber 488 and the size of channel 422. Rotation of spool 412 relative to handle 414 may dispense or retract optical fiber 488 from channel 422 through introducer 416 and guide 440, and spool 412 may be more quickly or efficiently rotated using hole crank 428 or indented portion 482.

In one aspect, optical fiber connector 490 may be connected to an energy source while positioned within coupler 472. Alternatively, optical fiber connector 490 may be connected to an energy source while positioned in one of connector clips 474. In another aspect, optical fiber connector 490 may be removed from coupler 472 to unwind and extend to an energy source. In this instance, a proximal portion of optical fiber 488 exposed from slit 484 may correspond to a distance from medical device 410 to the energy source. The disconnecting of optical fiber 488 to connect to the energy source may be done before or after dispensing the distal portion of optical fiber 488. In either aspect, medical device 410 may be kept sterile, while the proximal end connector 492 may connect to a non-sterile energy source without increasing the risks for the patient.

Figure 11:
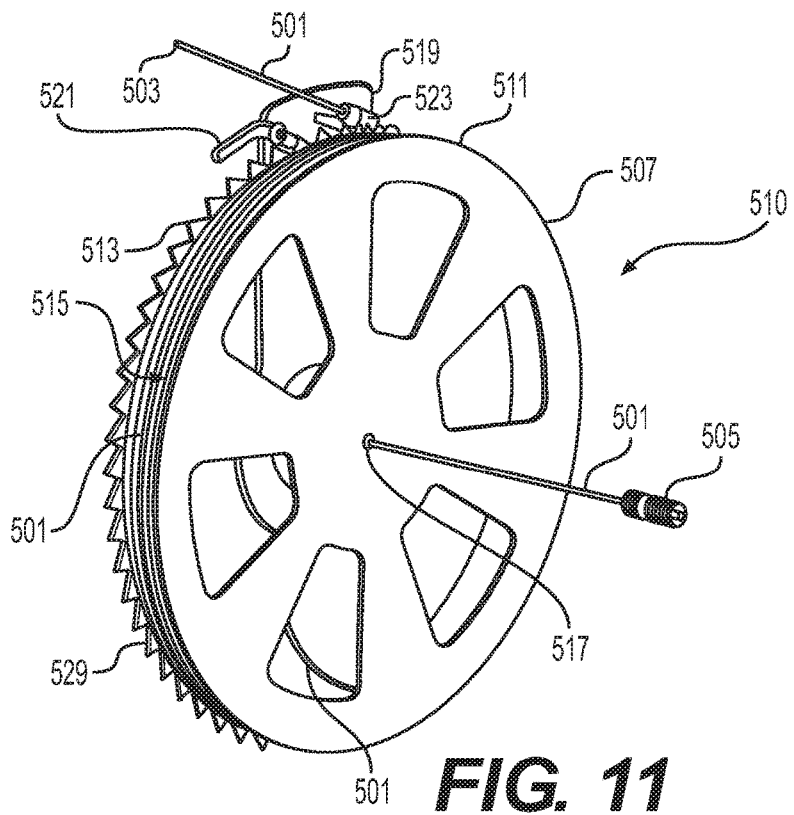
FIG. 11 illustrates an additional medical device, according to aspects of the present disclosure.
Figure 12:
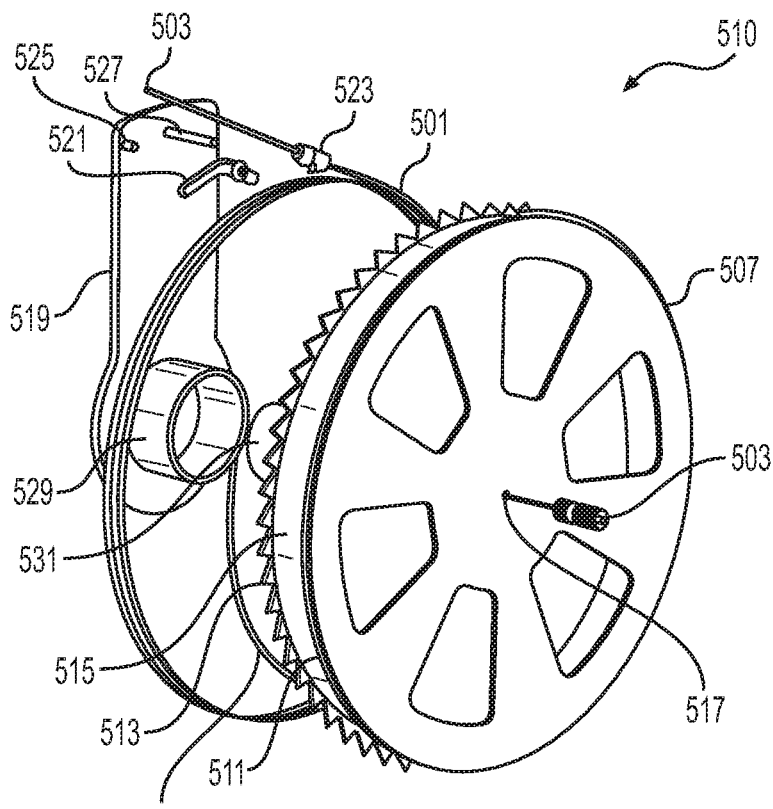
FIG. 12 illustrates a partially exploded view of the medical device of FIG. 11, according to aspects of the present disclosure.

Turning now to FIGS. 11-14, further aspects of this disclosure are detailed, with similar elements to medical device 10 shown by 500 added to the reference numbers. In particular, a medical device 510 is shown in FIG. 11, with a partially exploded view of medical device 510 shown in FIG. 12. Various additional aspects are detailed in FIGS. 13 and 14. Medical device 510 includes an optical fiber 501, including an optical fiber tip 503 and an optical fiber connector 505. Optical fiber tip 503 may be positioned within a patient to deliver energy, and optical fiber connector 505 may be coupled to a remote energy source (not shown). Medical device 510 also includes a disc 507, which may be rotatable and include a central pin 509 (shown in FIG. 13), a smooth edge 511, and a toothed edge 513. Smooth edge 511 and toothed edge 513 may form a groove 515. When assembled, optical fiber 501 may be wound around disc 507 in groove 515. Disc 507 may also include a central hole 517, which may be surrounded by central pin 509 (FIG. 13), and a portion of optical fiber 501 may pass through central hole 517, as shown in FIGS. 11 and 12.

Figure 13:
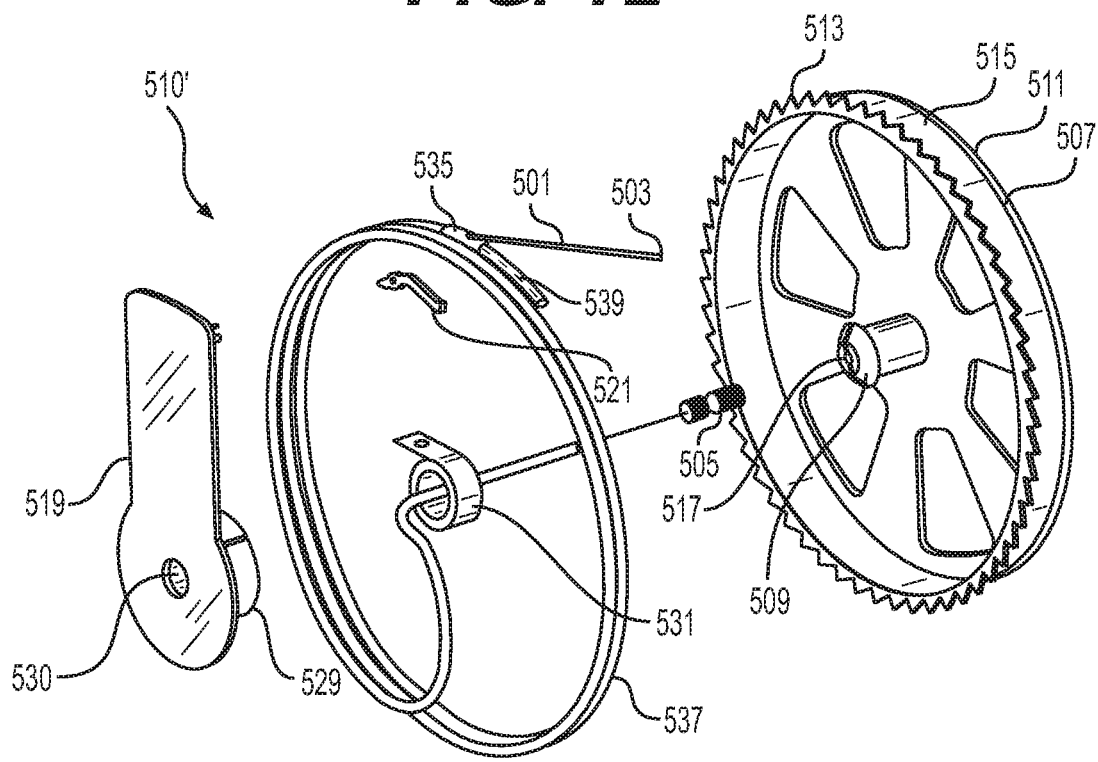
FIG. 13 illustrates a partially exploded view of an additional medical device, according to aspects of the present disclosure.

Medical device 510 also includes a spooler 519, a ratcheting lever 521, and a spooler cone 523. As shown in FIG. 12, spooler 519 may include a ratcheting lever pin 525 and a spooler cone pin 527, such that ratcheting lever 521 and spooler cone 523 may be coupled to spooler 519. Ratcheting lever 521 may selectively lock the rotation of disc 507 by interacting with toothed edge 513, and spooler cone 523 may surround a portion of optical fiber 501 to aid in preventing optical fiber 501 from tangling. Spooler 519 further includes a circular extension 529 with a spooler hole 530 extending through spooler 519 and circular extension 529 (FIGS. 12 and 13). A portion of optical fiber 501 extends from groove 515 behind spooler 519, through spooler hole 530 and central hole 517, and proximally to optical fiber connector 505.

As shown in the partially exploded views of medical device 510 in FIG. 12 and of medical device 510' in FIG. 13, medical devices 510 and 510' include a return spring 531. It is noted that return spring 531 is hidden in FIG. 11 and not fully visible in FIG. 12, but that the return spring 531 in FIG. 13 is the same as the hidden or partially hidden return spring 531 of FIGS. 11 and 12. Return spring 531 may be a constant force spring. When assembled, return spring 531 may surround and be fixedly attached to central pin 509. Central pin 509 may then be positioned within circular extension 529 to couple disc 507 to spooler 519, such that one end of return spring 531 is anchored to an inner face of circular extension 529 of spooler 519. Therefore, as disc 507 rotates relative to spooler 519, return spring 531 becomes increasingly stretched. Return spring 531 serves to bias the rotational motion of disc 507 relative to spooler 519. It is noted that since a proximal portion of optical fiber 501 passes through central hole 517, optical fiber 501 does not get twisted or otherwise interfered with as disc 507 rotates.

A user may dispense optical fiber 501 from medical device 510 by distally pulling optical fiber tip 503. As optical fiber 501 is pulled from groove 515, disc 507 rotates relative to spooler 519. Return spring 531 biases disc 507 to return to the original position, but ratcheting lever 521 locks into the teeth in toothed edge 513 to prevent disc 507 from returning. The user may pull optical fiber 501 until optical fiber tip 503 extends the length necessary to perform a medical procedure. After the medical procedure, or if the user wishes to retract optical fiber 501, the user may actuate ratcheting lever 521 to release ratcheting lever 521 from the teeth of toothed edge 513, which will then allow the force of return spring 531 to return disc 507 to its initial position relative to spooler 519. As disc 507 returns to its initial position, optical fiber 501 is drawn proximally and winds within groove 515. The user may release ratcheting lever 521 to stop the winding to reposition the distal length of optical fiber 501, or the user may allow the winding to continue until optical fiber 501 is totally wound and fully spooled around disc 507.

It is noted that, because optical fiber connector 505 extends proximal to disc 507 and the other components of medical device 510, optical fiber connector 505 may extend to be coupled to an unsterilized energy source. Moreover, the user may dispense and rewind optical fiber 501 on disc 507 within medical device 510 several times over the course of a medical procedure, all while maintaining a sterile field. Medical device 510 may also be within a casing, and casing may include actuators necessary to activate the components of medical device 510 discussed above. In addition, medical device 510 has been described as including optical fiber 501, but it is noted that the disclosure is not so limited, as medical device 510 may include a guidewire, bendable catheter, filament, cable, or other medical element.

Figure 14:
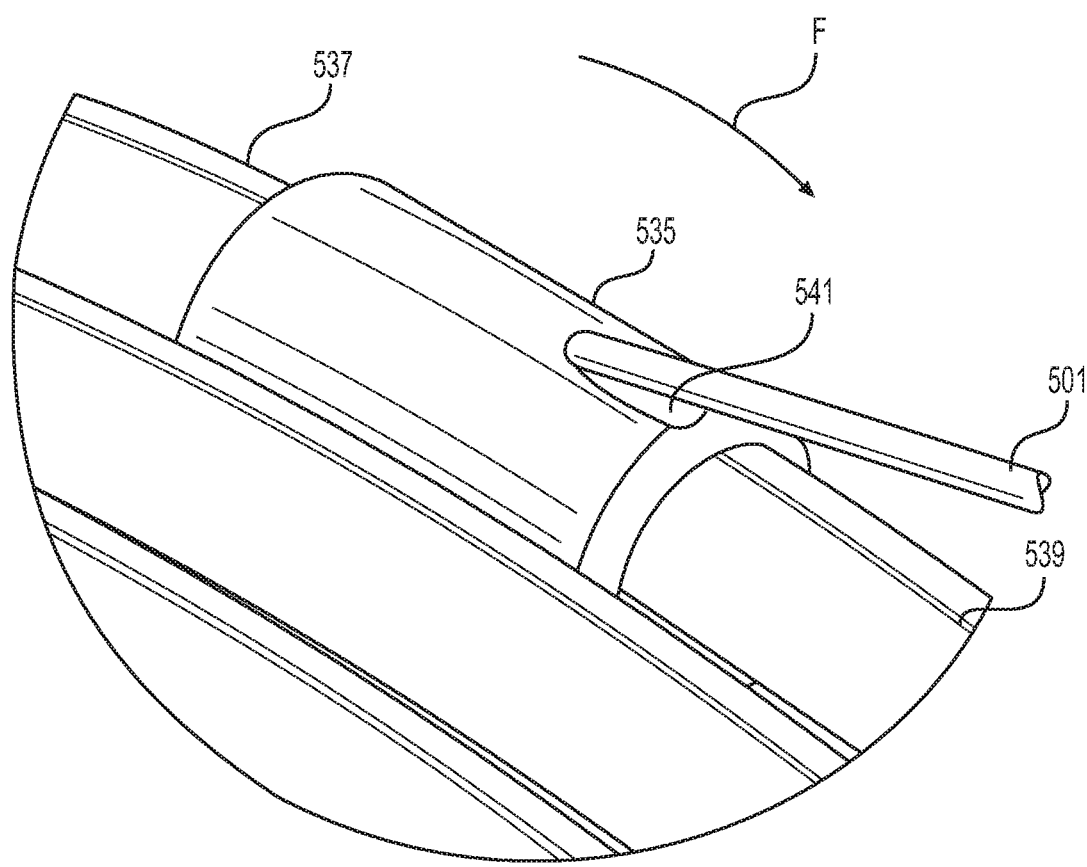
FIG. 14 illustrates a perspective view of a portion of the medical device of FIG. 13, according to aspects of the present disclosure.

As shown in FIGS. 13 and 14, medical device 510' may further include a zipper 535, which replaces spooler cone 523, and a zipper tube 537. Zipper 535 and zipper tube 537 may allow a user to selectively dispense and retract a portion of optical fiber 501 in both a proximal direction and a distal direction. Zipper 535 may be attached to spooler cone pin 527, and may radially and slidably surround zipper tube 537. Zipper tube 537 may surround the portion of optical fiber 501 internal to medical device 510. Zipper tube 537 may be positioned around disc 507, which may include toothed edge 513 and a smooth edge 511 to form a groove 515 to guide zipper 535 and zipper tube 537. Zipper tube 537 may rotate in unison with disc 507.

Zipper tube 537 may also include a tube slit 539 that extends longitudinally along at least a portion of zipper tube 537. Tube slit 539 may be a preformed gap or slit, may be perforated, or may be a portion of zipper tube with a decreased radial thickness. An end of zipper tube 537 on the periphery of disc 507 may be coupled to disc 507, and an opposite end of zipper tube 537 may pass through central hole 517 such that zipper tube 537 does not get twisted or otherwise interfere with the rotation of disc 507. The rotation of the zipper tube 537 relative to spooler 519 is biased by return spring 531.

As shown in FIG. 14, zipper 535 radially surrounds zipper tube 537, and includes a guide portion 541 through which the distal portion of optical fiber 501 may travel as the user pulls the distal portion to extend the optical fiber 501 toward the patient. It is noted that the biasing force is selectively balanced by ratcheting lever 521 locking in the teeth of toothed edge 513, as discussed above. As discussed above, the user may actuate ratcheting lever 521 to unlock the teeth of toothed edge 513 to retract optical fiber 501.

In one aspect, as the user pulls optical fiber 501 distally in direction F, zipper 535 rotates with the rotation of disc 507. Zipper 535 unzips zipper tube 537 and guides optical fiber 501 out of zipper tube 537 such that optical fiber 501 may continuously slide out of guide portion 541.

In another aspect, optical fiber 501 may include a proximal slack portion (not shown) similar to FIG. 10 that a user may employ to extend optical fiber connector 505 to the energy source. In either aspect, the user may pull optical fiber connector 505 proximally and either unwind or use the slack portion to connect optical fiber 501 to the energy source. Although not shown, medical device 510' may include exterior tabs to secure the length of the proximal portion of optical fiber 501. The user may then pull optical fiber tip 503 distally to reach the patient or the desired distance internal to the patient, for example, to apply energy to a kidney stone in laser lithotripsy. The distal portion of optical fiber 501 may be retracted and later dispensed again so long as medical device 510 is kept sterile and remote from the connection of optical fiber connector 505 to the non-sterile energy source. After the procedure, the user may use medical device 510' to rewind optical fiber 501 by actuating the ratcheting lever 521, pulling zipper 535, and/or rotating spooler 519.

The aspects of FIGS. 11-14 may also be incorporated in any of the other embodiments of this disclosure. Specifically, spooler 519, ratcheting lever 521, and return spring 531 may be incorporated with medical devices 10, 110, 110', 210, 310, and 410. As will be apparent to one having ordinary skill in the art, spooler cone 523 may be incorporated in introducer 16, and zipper 535 and zipper tube 537 may be incorporated within channel 22.

In the systems and methods described above, a user may operate any of the foregoing medical devices 10, 110, 110', 210, 310, 410, 510, and 510' with one or two hands. Additionally, it is noted that any of the foregoing medical devices 10, 110, 110', 210, 310, 410, 510, and 510' may be coupled to and used in conjunction with an insertion device. Alternatively, any of the foregoing medical devices may include features such as, for example, clips, Velcro, adhesive, clamps, ties, through holes, etc., to allow for a user to connect the medical devices to drapes, operation tables, surgical trays, an IV pole, or other elements commonly found in a surgical environment. Any of the medical devices may also be pre-packaged with an internal coiled element. Moreover, any of the foregoing medical devices may be disposable in that the medical device and its components may be disposed of after use with a particular patient. It is further noted that different lengths and sizes of guidewires 160 and optical fiber 501 may be useful for different medical procedures based on the distance to the treatment site, the distance between the patient and the energy source, and other procedure specific factors.

The systems and methods discussed herein may help to allow a user to dispense and/or retract a coiled element, such as a guidewire, optical fiber, catheter, filament, cable, or another shaft-like medical element. The user may dispense only a length of the coiled element necessary to reach the patient, connect one medical device to another medical device, connect one medical device to the patient, etc. The user may also retract the coiled element for use again during the medical procedure. Therefore, the length of the coiled element is adjustable throughout the procedure. Moreover, as discussed above, certain aspects of this disclosure allow a user to extend a proximal portion of the coiled element to an energy source or other medical device. Extending the proximal portion of the coiled element allows the user to maintain the medical device in a sterile environment, and the user may repeatedly dispense and retract the distal portion of the coiled element over the course of a procedure with reduced risks of contamination. Furthermore, if the coiled element is difficult to control, large, slippery, or otherwise cumbersome, the medical devices and methods discussed herein may help the user to handle, dispense, and retract the coiled element. Lastly, the devices and methods disclosed herein may help to reduce the number of medical professionals and the duration of the medical procedure.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

We claim:

1. A medical device, comprising:
   a spool element, including a channel to receive or store a coiled element, and at least one catch that forms a lock for the coiled element between the catch and an edge of the channel, wherein a proximal end of the coiled element is positioned between the catch and the edge of the channel;
   a handle element, wherein the handle element is coupled to the spool element and includes a lumen that at least partially opens into the channel; and
   an introducer coupled to the handle,
   wherein relative rotation of the spool element and the handle element dispenses or retracts the coiled element from the introducer.

2. The medical device of claim 1, wherein the channel is formed by an inner rim and an outer rim.

3. The medical device of claim 2, wherein the handle includes a guide element extending from the lumen and into the channel between the inner rim and the outer rim to guide the coiled element into the introducer.

4. The medical device of claim 3, wherein the inner rim includes a groove around an exterior circumference, and wherein the handle includes a retainer element that extends partially into the groove.

5. The medical device of claim 1,
   wherein the spool includes at least one tab, wherein the at least one tab extends over a top portion of the channel.

6. The medical device of claim 1, wherein the handle element includes a central opening to receive at least one finger of a user to hold the handle element stationary while manipulating the spool element;
   wherein the spool includes a crank or a hole crank; and
   wherein a radial exterior of the spool includes knurls.

7. The medical device of claim 1, wherein a width of the channel is less than two times the width of coiled element.

8. The medical device of claim 1, wherein the handle includes a radially protruding ring that encloses at least a portion of the channel; and
   wherein the spool includes at least one slot on a side opposite to the protruding ring.

9. The medical device of claim 1, wherein the handle includes a biased lock element including extension elements separated by slits.

10. The medical device of claim 1, wherein the spool includes at least one window cut through into the channel.

11. The medical device of claim 1, further comprising an extension tube between the handle and the introducer, and wherein the introducer includes a tapered portion.

12. A medical device, comprising:
    a spool element, including a channel formed by an inner rim and an outer rim; and
    a handle element, including at least one cover portion, wherein the at least one cover portion includes at least one extension portion extending into the channel and abutting the inner rim or the outer rim to couple the handle element to the spool, and wherein the handle element includes a lumen that at least partially opens into the channel; and
    an introducer coupled to the handle element,
    wherein the outer rim includes at least one slit extending along a portion of the outer rim transverse to the circumference of the outer rim, and
    wherein the handle element includes a guide element extending from the lumen and into the channel between the inner rim and the outer rim to guide a coiled element within the channel into the introducer.

13. The medical device of claim 12, wherein the slit extends transverse to the circumference of the outer rim and connects to a circumferential slit.

14. The medical device of claim 12, wherein the handle element includes at least two extension portions, wherein a first extension portion biasedly abuts the inner rim and a second extension portion biasedly abuts the outer rim, and wherein the inner rim and outer rim include grooves into which the first and second extension portions rotatably extend.

15. The medical device of claim 12, further including the coiled element within the channel, and wherein relative rotation of the spool element and the handle element dispenses or retracts the coiled element from the medical device.

16. The medical device of claim 12, wherein a central portion of the handle element includes a connector coupler, wherein the medical device further includes an optical fiber and an optical fiber connector, and wherein the optical fiber connector is lockably positioned within the connector coupler and a proximal portion of the optical fiber extends through one of the slits.

17. A medical device, comprising:
an optical fiber;
a spooler operably coupled to a ratcheting lever and including a circular extension with a spooler hole extending therethrough;
a disc including a toothed edge and a central pin, wherein the disc is engageable with the ratcheting lever, and wherein the central pin includes a central hole passing through the central pin;
a return spring positioned within the circular extension positioned between the spooler and the central pin;
wherein the optical fiber is looped around an external portion of the disc, and wherein a portion of the optical fiber passes through the spooler hole and the central hole.

18. The medical device of claim 17, further including a spooler cone pin attached to the spooler, wherein a distal portion of the optical fiber passes through the spooler cone pin.

19. The medical device of claim 17, wherein the disc further includes a smooth edge extending parallel to the toothed edge;
wherein a portion of the optical fiber is housed within a groove formed between the toothed edge and the smooth edge of the disc; and
wherein a portion of the optical fiber extends proximal to the groove such that the optical fiber is connectable to an energy source remote from the medical device.

20. The medical device of claim 17, further comprising a slitted tube and a zipper, wherein the zipper includes a guide portion through which a portion of optical fiber extends to move distally or proximally.

* * * * *